(12) United States Patent
Landschuetz et al.

(10) Patent No.: US 9,297,875 B2
(45) Date of Patent: Mar. 29, 2016

(54) MAGNETIC RESONANCE SYSTEM AND METHOD FOR TIME SYNCHRONIZATION OF DIFFERENT COMPONENTS OF A MAGNETIC RESONANCE SYSTEM

(71) Applicants: Wilfried Landschuetz, Baiersdorf (DE); Thorsten Speckner, Erlangen (DE)

(72) Inventors: Wilfried Landschuetz, Baiersdorf (DE); Thorsten Speckner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 799 days.

(21) Appl. No.: 13/630,258

(22) Filed: Sep. 28, 2012

(65) Prior Publication Data

US 2013/0082705 A1 Apr. 4, 2013

(30) Foreign Application Priority Data

Sep. 29, 2011 (DE) .......................... 10 2011 083 765

(51) Int. Cl.
*G01R 33/54* (2006.01)
*G01R 33/341* (2006.01)
*G01R 33/565* (2006.01)
*A61B 5/055* (2006.01)
*G01R 33/561* (2006.01)

(52) U.S. Cl.
CPC ............... *G01R 33/565* (2013.01); *A61B 5/055* (2013.01); *G01R 33/5617* (2013.01)

(58) Field of Classification Search
CPC .. A61B 5/055; G01R 33/5617; G01R 33/565; G01R 33/56572; G01R 33/5659; G01R 33/583
USPC .......................................... 324/307, 309, 318
See application file for complete search history.

(56) References Cited

U.S. PATENT DOCUMENTS

| | | | |
|---|---|---|---|
| 5,825,185 A | 10/1998 | Liu et al. | |
| 7,132,826 B1 * | 11/2006 | Jung | G01R 33/4824 324/307 |
| 7,327,141 B2 * | 2/2008 | Jung | G01R 33/4833 324/307 |
| 2007/0222446 A1 | 9/2007 | Jung et al. | |
| 2008/0061780 A1 | 3/2008 | Yamada et al. | |
| 2009/0267601 A1 | 10/2009 | Van Helvoort et al. | |

FOREIGN PATENT DOCUMENTS

CN 102096054 A 6/2011

OTHER PUBLICATIONS

Klaus Scheffler, "A Pictorial Description of Steady-States in Rapid Magnetic Resonance Imaging," Concepts in Magnetic Resonance, vol. 11 (5) (1999), pp. 291-304.

\* cited by examiner

*Primary Examiner* — Melissa Koval
*Assistant Examiner* — Rishi Patel
(74) *Attorney, Agent, or Firm* — Schiff Hardin LLP

(57) ABSTRACT

A method for time synchronization of various components of a magnetic resonance system includes generating a series of amplitude-modulated radio-frequency pulses and associated gradient fields to deflect the magnetization of a slice detecting at least two spin signals, determining a phase difference between two of the spin signals, processing the phase difference in order to determine at least one time shift between two of the following variables that are generated by different components of the magnetic resonance system, an envelope of the amplitude-modulated radio-frequency pulses, a radio-frequency portion of the amplitude-modulated radio-frequency pulses, and one or more gradient fields, and synchronizing the associated components of the magnetic resonance system depending on the at least one time shift.

10 Claims, 6 Drawing Sheets

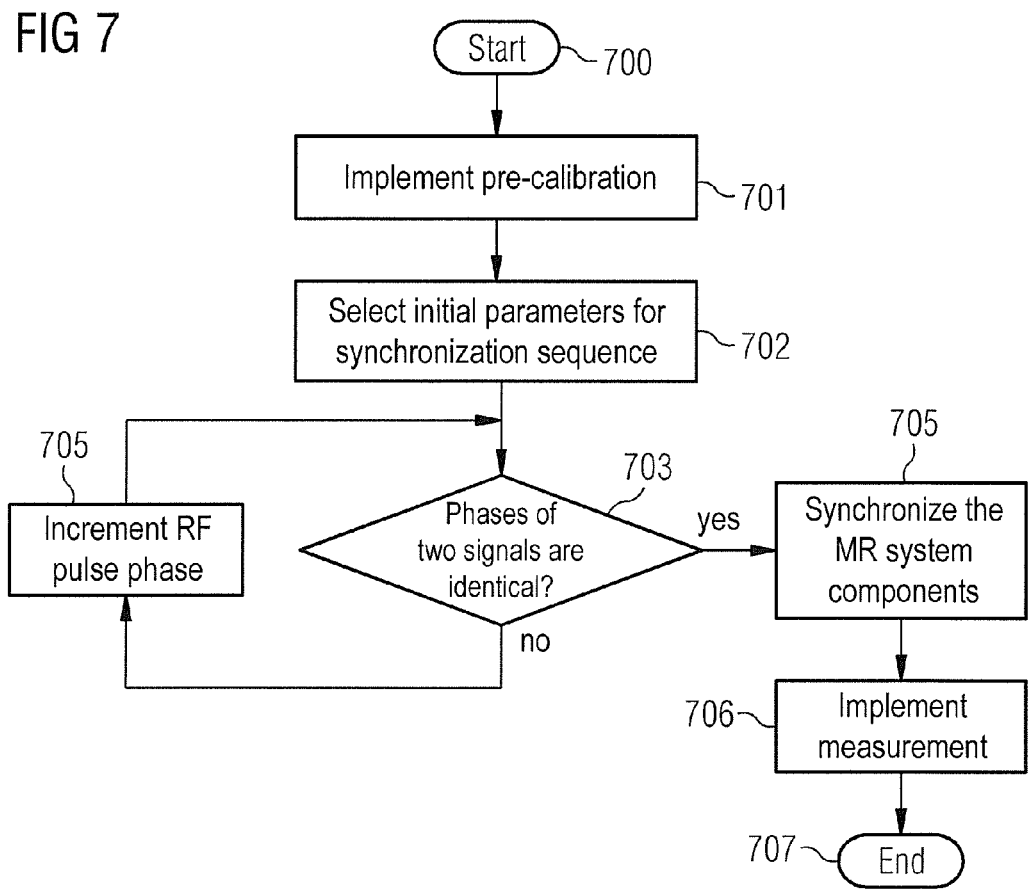

MAGNETIC RESONANCE SYSTEM AND METHOD FOR TIME SYNCHRONIZATION OF DIFFERENT COMPONENTS OF A MAGNETIC RESONANCE SYSTEM

BACKGROUND OF THE INVENTION

1. Field of the Invention

The present invention concerns a method for time synchronization of different components of a magnetic resonance system which interact in an acquisition sequence, and a magnetic resonance system for implementing such a method.

2. Description of the Prior Art

Magnetic resonance tomography is an imaging modality that is used for examination and diagnosis in many fields of medicine. It is based on the physical phenomenon of nuclear magnetic resonance. To acquire magnetic resonance (MR) signals, in an MR system, a static basic magnetic field is generated in the examination region, in which the nuclear spins or the magnetic moments of the atoms in the examination subject align. By means of an MR acquisition sequence, the nuclear spins can be deflected or excited out of the aligned position (i.e. the rest position) or another state by the radiation of radio-frequency pulses. The excited spin system can have a temporal dynamic.

The phase evolution of the spin system in the slice is described by the coherence curve. If the spins of a spin system of a defined slice all have an identical phase position, a magnetization signal with a large amplitude can be detected. A relatively strong signal can be detected since no destructive interference exists between the signals of different spins of different phase.

By applying a slice selection gradient upon radiation of the radio-frequency pulses, only nuclear spins are excited in a slice of the examination subject in which the resonance condition is satisfied due to the local magnetic field strength. Such a spatial coding can take place by application of a phase coding gradient as well as a frequency coding gradient during the readout. By slice-selective excitation it is possible to acquire MR exposures of multiple slices of an examined person.

Modern MR systems typically operate with distributed controls for the individual portions of an MR acquisition sequence. For example, a radio-frequency (RF) transmission system can include an RF generator and an amplitude modulation unit that respectively generate the radio-frequency portion or, respectively, the radio-frequency and the low-frequency amplitude modulation or, respectively, envelope of the RF pulses. A gradient system can generate the gradient fields for spatial coding.

The time synchronization of these components relative to one another is a basic requirement for a high quality of the MR imaging. With regard to conventional MR imaging it is already necessary to achieve such a high degree of time synchronization. However, there are additional fields of application in which the time synchronization is particularly important. For example, there is a significant interest in implementing the scanning scheme of k-space not only according to Cartesian MR imaging sequences but rather also according to a non-Cartesian scanning. Non-Cartesian scanning schemes have advantages, for example with regard to higher signal-to-noise ratio or better robustness with regard to movement of the examination subject. However Cartesian scanning is presently used nearly exclusively in clinical applications of MR imaging. The primary reason for this is that the realization of non-Cartesian k-space scanning schemes requires a more precise realization of the k-space trajectories then is the case for Cartesian scanning. This means that the degree of time synchronization of the various MR system components must be greater. In particular, it is known that a small time shift between the radio-frequency portion of an RF pulse and the envelope or the gradient fields is significant for the successful imaging by means of non-Cartesian scanning schemes of k-space.

An additional field in which a high degree of synchronization is necessary between the various MR system components is special RF pulses. By a special amplitude modulation of the associated gradient field for slice selection, such special pulses allow the spatial excitation profile to be designed so as to be particularly advantageous. It is thus possible to define the spatial excitation profile particularly sharply. Furthermore, by producing a uniform peak radio-frequency power it is possible to achieve a greater deflection angle of the magnetization from the steady state, and therefore to increase the signal-to-noise ratio given the same radio-frequency exposure. However, it is then necessary to temporally synchronize the gradient fields with the envelope and the radio-frequency portion of the RF pulses particularly precisely in comparison to conventional RF pulses.

For synchronization, methods can be used that enable relative time shifts of the individual components among one another to be measured directly in order to implement a calibration or time compensation based on these. For example, the rising edge of a gradient field is matched optimally precisely with the envelope of an RF pulse, or the envelope of the RF pulse is accordingly matched with the radio-frequency portion.

A synchronization of these different components conventionally takes place by means of a direct measured detection of the various component parameters, for example in the laboratory (what is known as error analysis). For example, in a design stage or development stage of the MR system the components can be affected such that the different timing signals are analyzed and the individual components are accordingly synchronized. It is thus possible to detect time shifts, for example with an oscilloscope or logic analyzer. Such methods have the disadvantage that different systematic errors can inherently occur due to deficiencies of this compensation measurement and of the compensation method. Such systematic errors are difficult to detect. It is thus not always possible to make all corresponding information of the tested components usable. Defined relevant temporal variables of a computer component for time control—for example a Field Programmable Gate Array (FPGA)—cannot be electronically tapped. Systematic errors can thus arise in the time synchronization: time shifts that have not been detected by the testing at the component level can occur in the implementation of an MR acquisition sequence. Furthermore, it is complicated to implement such methods for every MR system manufactured. A time shift that is MR system-specific and not specific to the model range can accordingly only be synchronized with difficulty by measures such as variation of cable lengths, for example.

Therefore, there is a need to provide an improved method for detection and compensation of a time shift of various components of a magnetic resonance system.

SUMMARY OF THE INVENTION

An object of the present invention is to provide a method and device that enable a time synchronization of various components of a magnetic resonance system.

According to a first aspect of the invention, a method for time synchronization of different components of a magnetic resonance system includes generating a series of amplitude-modulated radio-frequency pulses and associated gradient fields to deflect the magnetization of a slice, detecting at least two spin signals, determining, in a processor, a phase difference between two of the spin signals, processing the phase difference in order to determine at least one time shift between two of the following variables that are generated by different components of the magnetic resonance system to determine: an envelope of the amplitude-modulated radio-frequency pulses, a radio-frequency portion of the amplitude-modulated radio-frequency pulses, and one or more gradient fields, and synchronizing the associated components of the magnetic resonance system depending on the at least one time shift.

With RF pulses it is possible to deflect the magnetization of a slice, for example out of the steady state that is defined by a static basic magnetic field. In particular, these radio-frequency pulses can be associated with gradient fields so that the resonance condition that is necessary to deflect the magnetization is defined only for a defined location. If the magnetization is deflected out of the steady state, the magnetization can be described by a longitudinal component that points along the steady state and a transverse component that is perpendicular to the steady state. The transverse component of the magnetization precesses relative to the basic field. By suitable action on this transverse component it can be achieved that a spin signal arises. A spin signal arises by the rephasing of a previously dephased coherence curve of the transversal magnetization component.

If the coherence curve of a magnetization rephases, as explained above, a particularly strong spin signal arises. It is possible to inductively detect this spin signal, for example by means of radio-frequency coils. The detected signal has a defined phase. In particular, given multiple detected signals it is possible to determine by measurement a phase difference between the various signals. The phase difference is defined by the phase difference of the spin signals at the point in time of the complete rephasing. The point in time of the rephasing is most often also coincident with the point in time of maximum signal amplitude. The point in time of maximum amplitudes is associated with a rephased coherence curve. According to the present invention, it is then possible to calculate a time shift from the measured phase difference between at least two spin signals. The time shift can exist both between the envelopes of the amplitude-modulated radio-frequency pulses and the radio-frequency portion of the amplitude-modulated radio-frequency pulses and the associated gradient fields. For example, the envelope of the radio-frequency pulses is generated by a different module in the MR system than the radio-frequency portion itself. The radio-frequency portion is typically generated by numerically controlled oscillators (NCOs). By contrast, the amplitude modulation is generated by a conventional signal generator, for example, and mixed with the radio-frequency portion. Therefore it is necessary to synchronize these corresponding components of the MR system.

The time synchronization of various components of an MR system using MR data measured (acquired) in an MR acquisition sequence itself has advantages relative to methods that are based on achieving a time synchronization by measurement analysis of the different components. An implementation can thus take place wholly automatically in an operationally ready MR system. Furthermore, systematic errors due to unknown parameters can be minimized since a calibration occurs using MR data themselves. Since a synchronization takes place using actually acquired MR data, undetected, systematic measurement errors can be reduced. The synchronization takes place using data that are very similar to data acquired later in synchronization. Inaccuracies in the synchronization are reduced in such a manner.

Furthermore, it is possible to automatically implement such a method that is based on an MR acquisition sequence. It is not necessary to use external measurement apparatuses. In particular, it is possible to automatically verify the time synchronization from time to time in the operation of the MR system.

The radio-frequency pulses and the associated gradient fields may be generated such that the magnetization is deflected in the slice that us shifted by a predetermined distance relative to a reference slice at which the magnetization can be deflected by a reference frequency.

By the application of slice selection gradients in the form of gradient fields, it is possible for the RF pulses to be effective only at specific slices within the examination subject. This is because the spatially varying magnetic field causes (allows) the resonance condition of the magnetization to be satisfied only at a specific point or a specific slice within the examination subject. The magnetization can only be deflected there by means of RF pulses. In particular, it can be advantageous for such a slice selection gradient to be switched during the application of the RF pulses. In particular, it can be designed such that the magnetization is deflected in a slice that has a predefined distance relative to a reference slice. For example, the reference slice can be defined by a reference frequency. With respect to the reference slice, the gradient field is selected such that the magnetization can be deflected by a reference frequency since the reference frequency satisfies the resonance condition there. By the excitation of the magnetization in such a slice it is provided that the spin signals also show a dependency on the distance of the slice from the reference slice. It is thereby possible to deduce properties of the excitation pulses by the measurement of the signals with knowledge of (for example) the distance of the slice from the reference slice.

For example, in practice an NCO is configured so that it has a frequency shift relative to the reference frequency. For example, the reference frequency can be selected (for example dependent on the system) or can correspond (for example) to the resonance frequency of nuclear spins in water. This frequency shift is to be associated with a slice shift relative to the reference slice with knowledge of the switched gradient field. For example, the reference slice here designates a previously arranged slice defined with regard to the geometric dimensions of the MR system. Therefore, a defined region of the examination subject that is located in the MR system can be examined by the selection of the frequency shift (and of the gradient field).

Each radio-frequency pulse can have a respective deflection angle of the magnetization and a phase position can be associated therewith. The respective deflection angles are selected such that only a portion of the magnetization is deflected, and so that at least one of the following parameters assumes at least two different values as a result of the radio-frequency pulses and associated gradient fields: deflection angles of the radio-frequency pulses, phase positions of the radio-frequency pulses, and amplitudes of the gradient fields.

If only a portion of the magnetization is deflected by appropriate dimensioning of the deflection angle of an RF pulse out of the rest state, this is equivalent to a finite magnetization existing after application of an RF pulse. It is not the entire magnetization that is deflected in the transverse plane by the direction of the basic magnetic field. In other words, the RF pulses are selected such that they have a deflection angle smaller than 90°. A deflection angle of 90° is equivalent to the entire magnetization being flipped in the transverse plane.

If a shift of the radio-frequency of the RF pulse exists relative to a reference frequency, the phase position of the radio-frequency or the radio-frequency portion thus varies relative to the reference frequency as a function of time. This is designated as a phase response. The phase position of an RF pulse is accordingly advantageously defined relative to the reference frequency at the temporal center point of the envelope of the radio-frequency excitation pulse.

For example, it can be advantageous for the deflection angles of at least two radio-frequency pulses to assume different values. This means that the deflection angle (for example in a first radio-frequency pulse) assumes a different value than in a second radio-frequency pulse, and therefore the proportion of the magnetization that is flipped out of the longitudinal in the transverse plane assumes different values. It is also possible for the phase positions of at least two RF pulses to assume different values. It can accordingly be possible that the amplitudes of two gradient fields assume different values.

The alternating different selection of the various parameters takes place so that an equation system which enables the determination of different parameters of the excitation pulses with regard to the measurement and known variables of the signals or acquisition sequence is sufficiently determined. For example, if all excitation pulses or gradient fields are dimensioned identically, it is possible that the equation system is underdetermined. This would limit the determinable parameters of the excitation pulses.

However, in this regard it is also possible that—as a result of the radio-frequency pulses and associated gradient fields—at least one of the following parameters assumes the same value at least twice: deflection angles of the radio-frequency pulses, phase positions of the radio-frequency pulses, and amplitudes of the gradient fields.

If specific parameters of the acquisition sequences are selected identically, this simplifies the underlying equation system. The number of variables is reduced. It must be ensured that the number of variables is not reduced so far that the equation system is underdetermined, i.e. cannot be unambiguously solved.

The method can furthermore include incrementally varying a phase position of at least one radio-frequency pulse to minimize the phase difference in order to determine the at least one time shift.

It can be advantageous to charge a phase of an RF pulse by means of an additionally introduced phase instead of measuring the phase difference between two radio-frequency pulses once, and from this to directly determine the time shift. The additionally introduced phase can be varied incrementally until the phase difference between two spin signals is minimized or disappears. This is the case since the phase difference between two spin signals typically depends on the additional phase introduced by an radio-frequency pulse. Such a method can be advantageous since it can be implemented wholly automatically. It is possible to correspondingly configure an MR system so that the phase position of a defined RF pulse is successively varied within the scope of a calibration sequence until a defined criterion (minimization of the phase difference) is achieved. In particular, it is possible to provide the desired temporal resolution in the determination of the time shift by the suitable selection of the incrementing of the phase. By a smaller incrementing of the phase of an RF pulse it is accordingly possible to determine the time shift with more precision.

As explained above, an automatic implementation has the advantage of making it possible to implement such a synchronization frequently. The automatic implementation within the scope of calibration routines allows an equally high degree of time synchronization to always be ensured over the service life of an MR system. In particular, it is possible to detect system errors (which result in a time shift of the individual components, for example) early. A decrease of the time synchronization over the operating period of an MR system thus can be corrected.

It can be advantageous for the magnetization to be deflected by first, second and third radio-frequency pulses with associated first, second and third gradient fields, and for the spin signals to be respectively detected as first and second spin echoes and a stimulated spin echo.

Such a special embodiment of the present invention is based on the fact that three RF pulses are used in order to deflect the magnetization. If the RF pulses have respective deflection angles that deflect only a portion of the longitudinal magnetization in the transverse plane (meaning that the deflection angle is smaller than 90°), a first spin echo and a second spin echo and a stimulated spin echo thereby arise.

For example, it is possible that the spin echoes arise by the dephasing by means of suitably switched (activated) gradient fields and by the subsequent refocusing by means of a radio-frequency pulse and additional suitably switched gradient fields. The coherence curve of the transverse magnetization component here is initially dephased by a first gradient field. This means that the individual spins subsequently have different phase positions. No signal can be detected since destructive interference occurs between the spins. An additional RF pulse can act as a refocusing pulse on the spin system. The coherence curve of the spin system is inverted. A subsequently switched gradient field of suitable algebraic sign and magnitude can then produce a rephasing of the coherence curve. Given a disappearing dephasing of the corresponding coherence curve, a spin echo occurs.

Given three RF pulses, multiple spin echoes can be detected. In addition to these spin echoes, it can be advantageous to also use what are known as stimulated echoes for the time synchronization. For example, a stimulated spin echo can arise from a portion of the magnetization that was initially deflected in the transverse plane by a series of RF pulses, has subsequently been deflected back in the longitudinal direction and was ultimately deflected again in the transverse plane by generation of a stimulated spin echo.

If three RF pulses are used, the use of a stimulated spin echo and two spin echoes can have the advantage that the signal amplitudes of the corresponding spin signals are sufficiently high. The higher the signal amplitude of the various spin signals, the more precisely that a phase difference between two spin signals can be determined. However, a more precise determination of the phase difference between two spin signals has the result that the time shift of various components of the MR system can be determined more precisely.

The first gradient field can have a first gradient amplitude and the second and third gradient fields can have a second, different gradient amplitude.

If the gradient amplitude of the second and third gradient fields, which are respectively associated with the second and third RF pulses, are selected to be equally large, it is thus possible to derive or determine the phase difference of two spin signals (and therefore the time shift) by means of particularly simple calculation operations. The arising equation system is simplified by the same dimensioning of the second and third gradient fields, and it is possible to directly determine the initial parameters of the RF pulses from the phase difference between two spin signals.

A first time shift between the envelope of the amplitude-modulated radio-frequency pulses, and the radio-frequency portion of the amplitude-modulated radio-frequency pulses can be calculated as:

$$dT1=dPHI/(2D(Gs2-Gs1)\gamma),$$

wherein dPHI is the phase difference between the phase of the second detected spin echo and the phase of the stimulated spin echo; wherein D is the distance of the slice from the reference slice; and wherein γ is the gyromagnetic ratio; wherein the phase positions of the first and second radio-frequency pulse are selected identically. The first time shift can be defined by the time interval between the beginning of the amplitude modulation signal and the insertion of the radio-frequency portion.

It is also possible to calculate a second time shift between the gradient fields and the radio-frequency portion of the amplitude-modulated radio-frequency pulses as:

$$dT2=dPHI/(D(Gs2-Gs1)\gamma),$$

wherein dPHI is the phase difference between the phase of the second detected spin echo and the phase of the stimulated spin echo, wherein D is the distance of the slice from the reference slice, and wherein γ is the gyromagnetic ratio. The second time shift can be defined by the time interval between the beginning of the amplitude modulation signal and the beginning of the slice selection gradient.

By the particularly simple selection of three RF pulses and two gradient fields of the same amplitude that belong to the second and third RF pulses as described above, it is possible to directly calculate the first and second time shifts corresponding to the above formulas. In particular, only the known magnitude of the amplitudes of the gradient fields Gs1 and Gs2, the known gyromagnetic ratio, the known shift D of the slice relative to the reference slice and the measured phase shift enter into the calculation.

It can be advantageous to initially minimize the phase shift between the spin signals for calculation of the time shift by (as explained above) incremental variation of a phase of an RF pulse. In combination with the above formulas, this allows a particularly simple determination of the first and second time shift.

According to a further aspect of the invention, a magnetic resonance system has a radio-frequency signal generator to generate a radio-frequency portion of an amplitude-modulated radio-frequency pulse, an amplitude modulation unit to generate an envelope of an amplitude-modulated radio-frequency pulse, a gradient unit to apply a gradient field overlapping in time with the amplitude-modulated radio-frequency pulse, and a radio-frequency reception system to detect spin signals. The radio-frequency transmission system is configured to generate a series of amplitude-modulated radio-frequency pulses and associated gradient fields to deflect the magnetization of a slice; and wherein the radio-frequency reception system is configured to detect at least two spin signals. The magnetic resonance system furthermore has a calibration unit that is configured to determine a phase difference between two of the spin signals; to process the phase difference in order to determine at least one time shift between two of the following variables that are generated by different components of the magnetic resonance system: an envelope of the amplitude-modulated radio-frequency pulses, a radio-frequency portion of the amplitude-modulated radio-frequency pulses, and one or more gradient fields, and to synchronize the associated components of the magnetic resonance system depending on the at least one time shift.

An MR acquisition sequence typically has various elements such as gradient fields and radio-frequency pulses. These elements are generated by the discussed various components of an MR system. For example, the RF signal generator can be a numerically controlled oscillator (NCO). The amplitude modulation of the radio-frequency portion can occur by mixing the signal of the NCO with the output signal of the amplitude modulation unit. The gradient unit can include a gradient system to generate spatially varying magnetic fields.

The advantages of the magnetic resonance system according to the invention correspond to those described above with regard to the method.

BRIEF DESCRIPTION OF THE DRAWINGS

FIG. 7 is a flowchart of an embodiment of a method to synchronize various components of an MR system in accordance with the invention.

DESCRIPTION OF THE PREFERRED EMBODIMENTS

Figure 1:
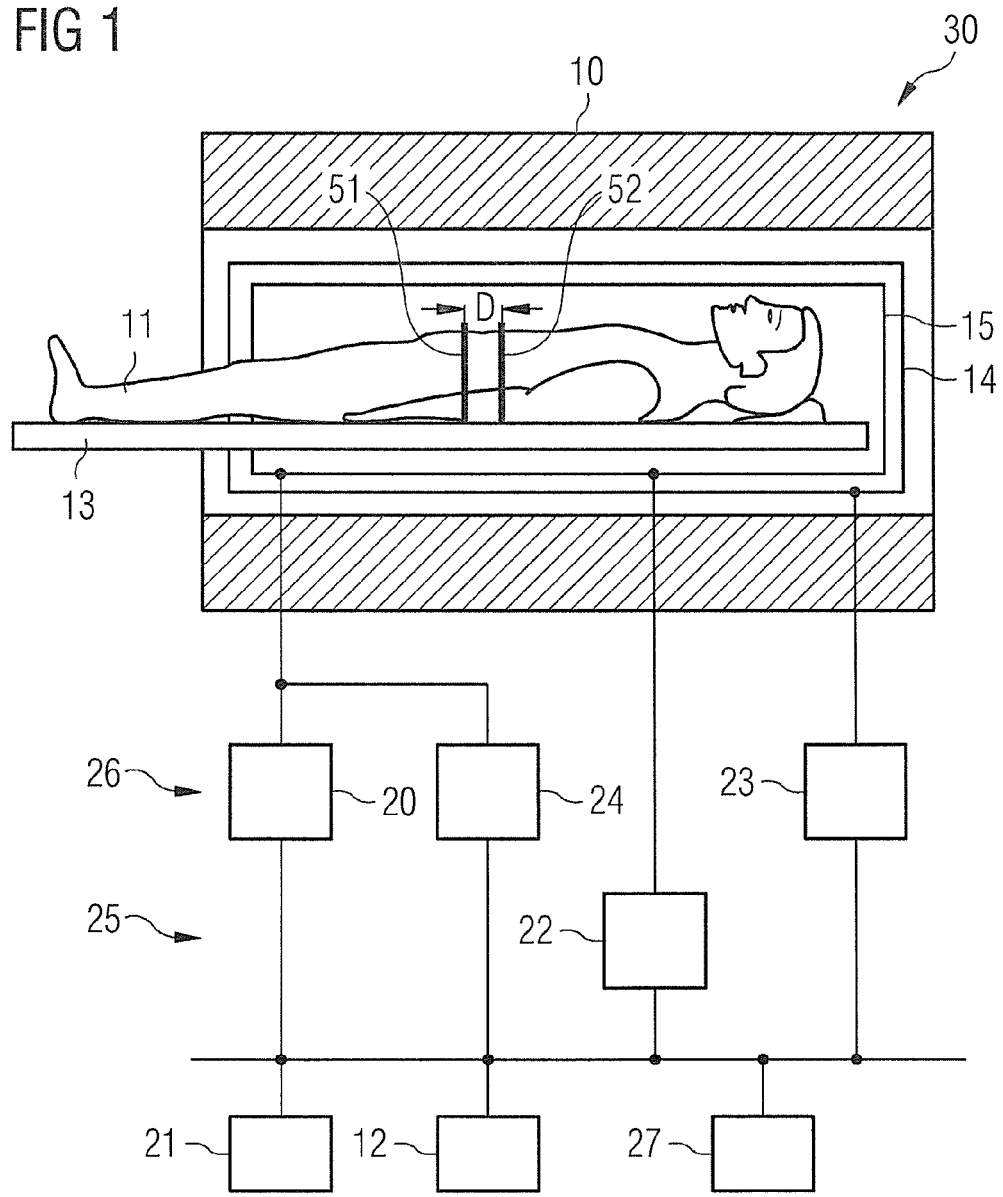
FIG. 1 schematically illustrates a magnetic resonance system according to the present invention.

FIG. 1 schematically shows a magnetic resonance system 30 configured to acquire magnetic resonance (MR) data. The MR system can have one or more radio-frequency (RF) antennas (radiators) 15. The MR system 30 furthermore has a basic field magnet 10 that generates a basic magnetic field. An examination subject—in the shown case an examined person 11—can be moved into the magnet 10 by a bed 13.

The basic magnetic field generated by the magnet 10 polarizes the nuclear spin system. In its rest position, the spins are oriented along the direction of the basic magnetic field. With the RF coil 15, a radio-frequency (RF) pulse can be generated that deflects the magnetization out of its rest state in the basic magnetic field. A radio-frequency generator 20 and an amplitude modulation unit 24 are provided for radiation of the radio-frequency pulses by the radio-frequency coil 15. The radio-frequency generator 20 typically includes a numerically controlled oscillator (NCO). The amplitude modulation by the amplitude modulation unit 24 is necessary in order to achieve a targeted spatial excitation profile of the magnetization.

Furthermore, the MR system 30 has a gradient system 14 configured to provide magnetic field gradients in the region of the examined person 11. Magnetic field gradients or gradient fields produce a spatial coding of the signals resulting from the excitation of the nuclear spins provided by the RF pulses due to the resonance state of the spin systems. The magnetization can be deflected only in a slice 52 that is shifted by a distance D relative to a reference slice 51. Therefore, gradient fields are also typically applied in parallel with the RF pulses. A gradient unit 23 controls the time sequence and the parameters of the gradient fields. The RF signal generator 20, amplitude modulation unit 24 and gradient unit 23 form a radio-frequency transmission system 26.

Furthermore, a magnetization signal that inductively causes a voltage in the radio-frequency coil 15 can be detected by a radio-frequency reception system 25 in the form of a computer 22. An operating unit 12 is connected with the control elements and allows a user to implement the control of the magnetic resonance system 30.

It is necessary to ensure synchronization of the components of the RF transmission system 26, i.e. the RF signal generator 20, the amplitude modulation unit 24 and the gradient unit 23 within the scope of an MR acquisition sequence. For example, if the RF signal generator 20 and the amplitude modulation unit 24 are synchronized with regard to a first time shift, it is then ensured that the radio-frequency portion of an RF pulse is matched with the envelope of the RF pulse in a later MR acquisition sequence. Additional phases that were impressed on the spin system due to such a time shift are thereby prevented. Furthermore, given matching and time synchronization of the gradient unit 23 and the amplitude modulation unit 24, it is ensured that gradient fields switched during an MR acquisition sequence are temporally synchronous with the envelope of the various RF pulses. An additional phase impressed on the spin system is thereby suppressed.

The general functioning of an MR system is known to those skilled in the art, so a more detailed description of the general components is not necessary herein.

Figure 2:
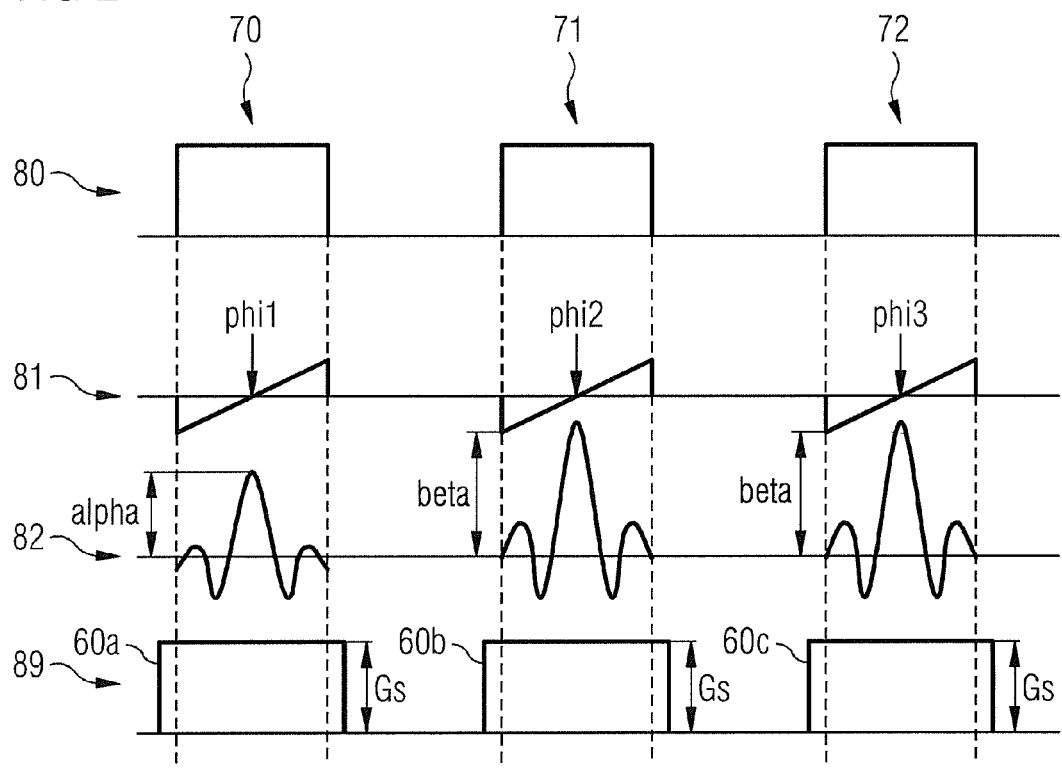
FIG. 2 schematically illustrates the radio-frequency pulses of an MR acquisition sequence for time synchronization of various components of an MR system.

The RF pulses of an MR acquisition sequence to determine the time shift between various components of the MR acquisition sequence are presented in FIG. 2. Three RF pulses 70, 71, 72 are applied in chronological sequence. The RF pulses 70, 71, 72 have an envelope 82 and a radio-frequency portion 80. Slice selection gradients 89 are used for slice selection. The radio-frequency portion 80 is typically generated by a numerically controlled oscillator (NCO) in the form of an RF signal generator. The slice selection gradients have the form of gradient fields 60a, 60b and 60c. These gradient fields ensure that the resonance condition under given radio-frequency portion 80 is ensured only for a defined slice of the examination subject. This is the case since the local magnetic field strength spatially changes within the scope of the gradient fields 60a, 60b, 60c. The gradient fields 60a, 60b, 60c are typically applied optimally simultaneously with the envelope 82 and the radio-frequency portion 80. The amplitude modulation of the RF pulses 70, 71, 72 can thus take place in the form of a sinc pulse. This has the advantage of a defined spatial excitation profile of the RF pulse. The sinc-like envelope or amplitude modulation is graphically indicated in FIG. 2. It is also possible to select other forms of amplitude modulation.

The three RF pulses are respectively characterized by phase positions phi1, phi2, phi3 and deflection angles alpha, beta. The phase position phi1, phi2, phi3 of the RF pulse is defined by the phase shift of the radio-frequency relative to a reference frequency at the temporal middle point of the envelope 82 of the radio-frequency excitation pulse. For example, the reference frequency can be selected depending on the system or can correspond to the resonance frequency of nuclear spins in water, for example. If an RF pulse is applied to deflect the magnetization, in practice its radio-frequency portion 80 is mostly defined by a difference frequency of relative to the reference frequency. Furthermore, the deflection angle is defined as the flip angle of the magnetization out of the longitudinal direction (defined by the basic magnetic field) in the plane transversal to this. The deflection angle can be proportion to the amplitude of the RF pulses 70, 71, 72, wherein diverse methods are also known to increase the deflection angle given constant amplitude.

The phase position of the radio-frequency portion 80 of the RF pulse thus changes as a function of time relative to the reference frequency. This is indicated by the phase response 81 in FIG. 2. A larger (smaller) difference frequency hereby results in a stronger (weaker) change of the phase response 81 as a function of time. In particular, in FIG. 2 a case is shown in which the deflection of the magnetization occurs in a slice that is shifted by a predetermined distance D relative to a reference slice. The reference slice can be defined, for example, as the slice in which the resonance frequency of the magnetization is the reference frequency. For example, the distance D then results from the shift of the radio-frequency portion 80 relative to the reference frequency. To deflect the spins in the slice it is therefore necessary to apply a gradient field as a slice selection gradient 89. This occurs within the scope of the gradient fields 60a, 60b, 60c that can all have an amplitude Gs. The amplitude Gs of the gradient fields hereby designates the rate of spatial change of the magnetic field strength. The radio-frequency of the RF pulses is then determined by the following equation, which characterizes the shift δf relative to the reference frequency:

$$\Delta f = D * Gs * \gamma,$$

wherein γ designates the gyromagnetic ratio. As explained above, a linear phase response 81 according to Δf*t arises, wherein t designates time.

Figure 3:
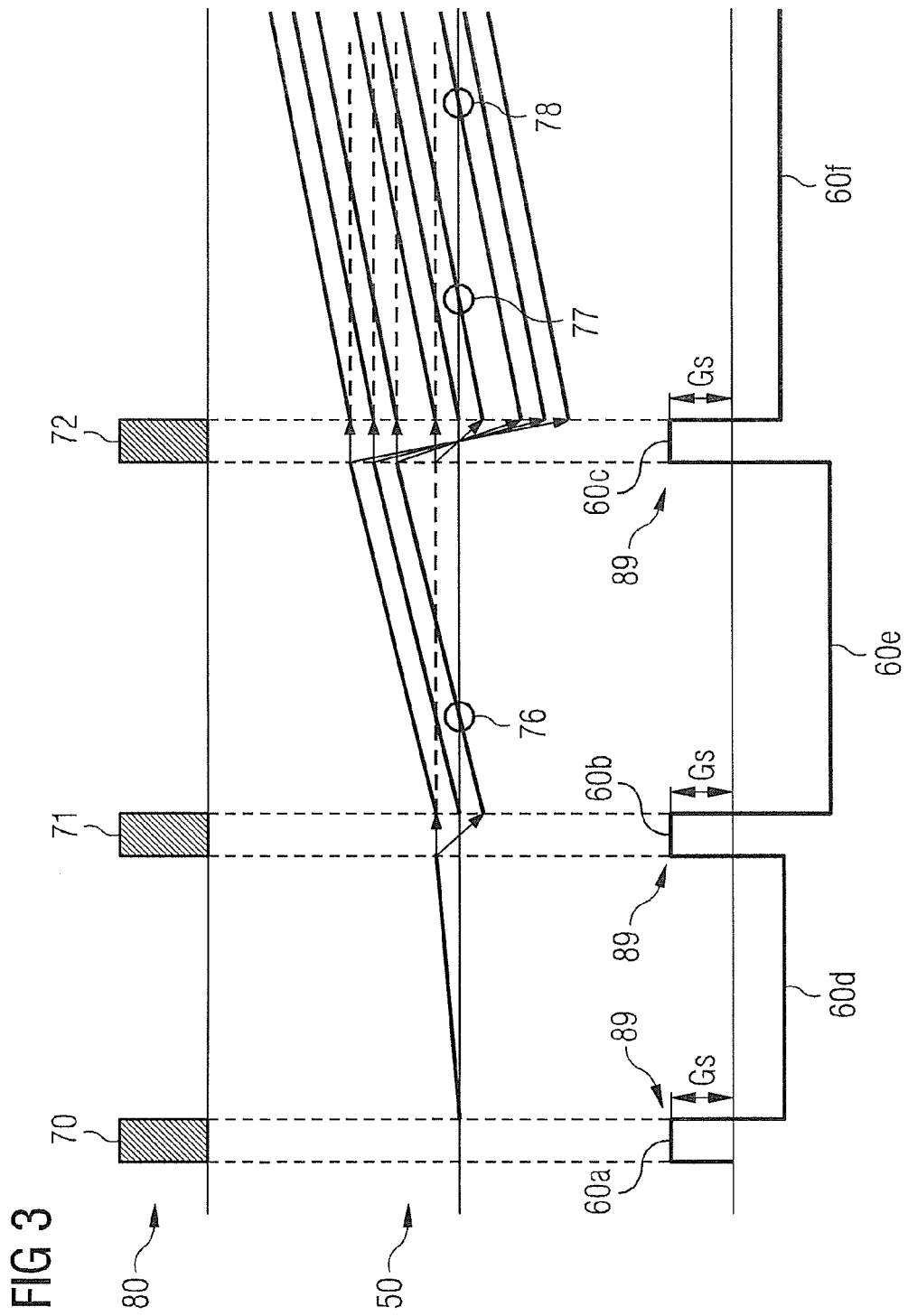
FIG. 3 schematically illustrates an MR acquisition sequence for time synchronization of various components of an MR system.
Figure 4:
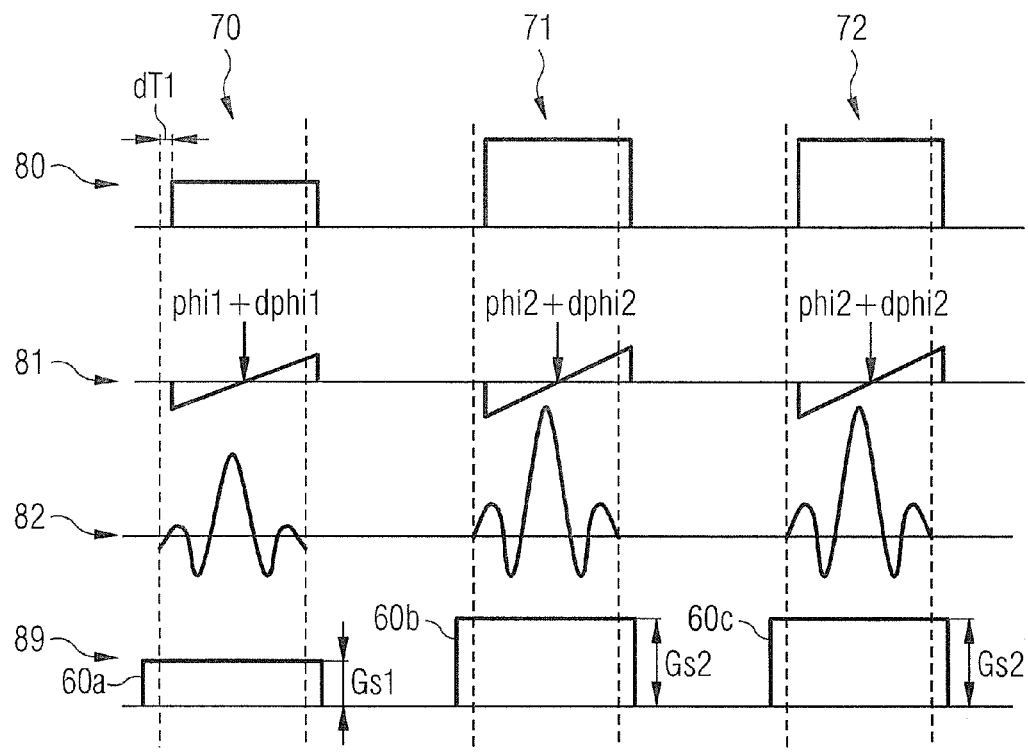
FIG. 4 schematically illustrates the radio-frequency pulses of an MR acquisition sequence for time synchronization of various components of an MR system, wherein a first time shift between the radio-frequency portion and the envelope the RF pulses is depicted.
Figure 5:
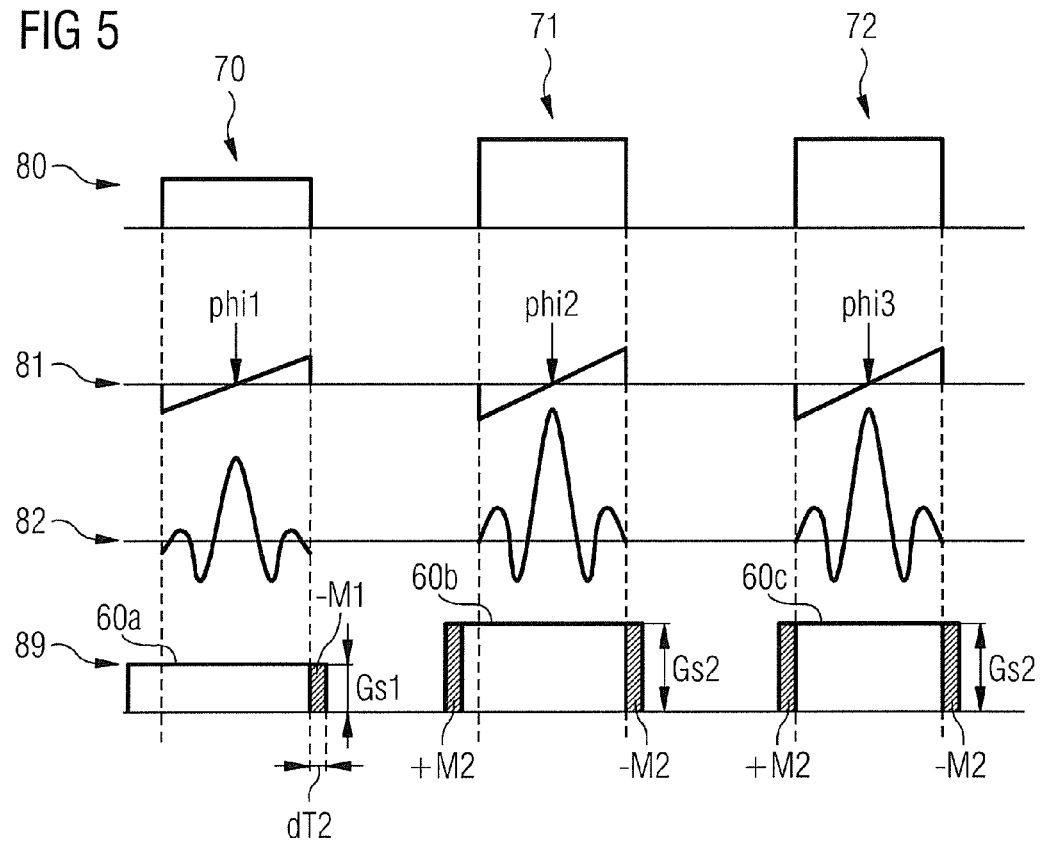
FIG. 5 schematically illustrates the radio-frequency pulses of an MR acquisition sequence for time synchronization of various components of an MR system, wherein a second time shift between the envelope of the RF pulses and the gradient fields is depicted.
Figure 6:
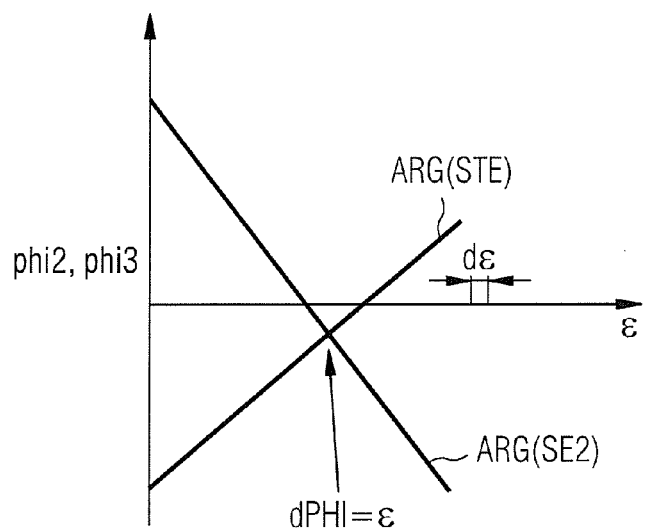
FIG. 6 schematically illustrates minimization of the phase difference between two spin signals.

With regard to a time synchronization of the various components of an MR system, as is explained in detail in regard to following FIGS. 4-6 it can be helpful for the deflection angle to be selected to be the same for different RF pulses. For example, the first RF pulse 70 can have a deflection angle alpha and the second and third RF pulse 71, 72 respectively have a deflection angle beta. This has the advantage that the calculation of the spin signal amplitudes is markedly simplified, as is discussed in the following with regard to FIG. 3.

An MR acquisition sequence to determine the time shift between various components of the MR acquisition sequence is shown in FIG. 3. In particular, the positions of the spin signals 76, 77, 78 are shown in the time curve relative to the excitation pulses 70, 71, 72. The excitation pulses 70, 71, 72 correspond to the excitation pulses as they were discussed in the preceding with regard to FIG. 2 are graphically represented by the radio-frequency portion 80.

Furthermore, the associated gradient fields 60a, 60b, 60c of the slice-selection gradients 89 are indexed. These gradient fields 60a, 60b, 60c with amplitudes Gs should advantageously be temporally synchronous with the RF pulses 70, 71, 72. As is apparent from FIG. 3, additional gradient fields 60d, 60e are switched between the various RF pulses 70, 71, 72. These gradient fields have the object of producing a dephasing or, respectively, rephasing of the transversal magnetization component. This is described by the coherence curve 50. The coherence curve 50 is shown in FIG. 3. This is explained in detail in the following order to also explain the various arising spin signals 76, 77, 78.

The first RF pulse 70 deflects a portion of the magnetization—that has up to that point been located in the steady state (longitudinal magnetization)—out of the steady state and thereby generates a transverse component. A dephasing of the transverse component during the application of the RF pulses 70, 71, 72 can be ignored. The transverse component is dephased by the switched gradient field 60*d* after application of the first RF pulse. This is graphically apparent by a rise of the coherence curve 50 between a first RF pulse 70 and before the second RF pulse 71.

The second RF pulse 71 subsequently affects the spin system. This second RF pulse 71 has various effects. A first effect causes a portion of the already existing transversal magnetization to be folded back into the longitudinal direction. This temporary part of the longitudinal magnetization is graphically represented in FIG. 3 with dashed lines between the second RF pulse 71 and the third RF pulse 72. The gradient field 60*e* produces no rephasing or dephasing of this portion of the magnetization since the gradient field does not have an effect on the static, non-precessing longitudinal portion. An additional effect of the RF pulse 71 is that a portion is folded out of the pre-existing longitudinal magnetization, into the transverse component. This newly generated transverse component of the magnetization has a coherence curve 50 that has a disappearing dephasing immediately after the second RF pulse 71. The third effect of the RF pulse 71 is that a portion of the already existing transversal magnetization is inverted, what is known as refocusing. The coherence curve 50 of this portion of the magnetization respectively has a different algebraic sign of the dephasing before and after the second RF pulse 71. This portion of the magnetization is rephased by gradient field 60*e* and generates a spin signal 76 between the second RF pulse 71 and the third RF pulse 72. This spin signal 76 is designated as a spin echo since it arises from the rephasing of an initially dephased magnetization component. Furthermore, it is noted that there is no effect on a portion of the transversal magnetization of the second RF pulse 71 that is generated by the first RF pulse 70.

The third RF pulse 72 has the same effects as described in connection with the second RF pulse 71. In particular, the portion of the magnetization that is flipped back in the longitudinal direction by the second RF pulse 71 is also flipped back in the transverse plane by the third RF pulse 72. This portion of the magnetization generates a stimulated spin echo 77. Furthermore, a secondary spin echo 78 is generated. Additional spin echoes are generated at points in time that are no longer shown in FIG. 3. Nevertheless, these higher spin echoes (for example the third and fourth spin echo) could also be used to implement a method for synchronization of different components of an MR system as they are described in the following.

It can be advantageous to dimension the various gradient fields 60*d*, 60*e*, 60*f* that are used for dephasing or rephasing such that the stimulated spin echo 77 and the secondary spin echo 78 occur at different points in time. In the exemplary embodiment of FIG. 3 this is ensured in that the gradient field 60*e* (which is switched between the second RF pulse 71 and the third RF pulse 72) has a different amplitude than the gradient fields 60*d* and 60*f*. This results in the rate of dephasing between the second RF pulse 71 and the third RF pulse 72 being greater than the rate of the dephasing (rephasing) between the first RF pulse 70 and the second RF pulse 71, as well as after the third RF pulse 72. This is graphically indicated by the slope of the coherence curve 50. Other dimensions of the gradient fields 60*d*, 60*e* and 60*f* for dephasing (rephasing) of the coherence curve 50 are possible.

The implementation of an MR acquisition sequence with three RF pulses 70, 71, 72 that respectively have a deflection angle of the magnetization that is smaller than 90° and accordingly have the above described effects on the coherence curve 50 is known in the literature. The properties of the spin signals 76, 77, 78 can be calculated. Such calculation—for example using Scheffler, Concepts in Mag. Res. 11 (1999) 291-304—the magnetization vectors M1, M2, M3 of the individual spin signals 76, 77, 78 thus yield:

Magnetization of the First Spin Signal 76, i.e. First Spin Echo SE1:

$$M1=\sin(\text{alpha})*i*\text{EXP}(-i(phi1-2*phi2))*(\sin(\text{beta}/2))^2.$$

wherein i designates the imaginary unit, EXP designates the exponential function, and sin designates the sin function.

Magnetization of the Third Spin Signal 78, i.e. Second Spin Echo SE2:

$$M3=\sin(\text{alpha})*(-i)*\text{EXP}(iphi1)*(\sin(\text{beta}/2))^4.$$

Magnetization of the Second Spin Signal 77, i.e. Stimulated Spin Echo STE:

$$M2=\sin(\text{alpha})*0.5*i*\text{EXP}(-i(phi1-phi2-phi3))*(\sin(\text{beta}/2))^2$$

The secondary spin echo SE2 is thus exclusively dependent on the phase of the first RF pulse phi1. The stimulated echo STE shows a dependency on phi1, phi2 and phi3. It is possible to select the phases of the RF pulses according to the following:

$$phi1=0,$$

$$phi2=phi3=90°(\pi/2).$$

It results from this that the primary and secondary spin echoes SE1, SE2 and the stimulated echo STE are oriented in parallel. This is used in the following with regard to FIGS. 4-6.

The RF pulses of an MR acquisition sequence to determine the time shift between various components of the MR acquisition sequence are shown in FIG. 4. The RF pulses correspond to the RF pulses discussed with regard to FIGS. 2 and 3. However, in FIG. 4 the beginning of the radio-frequency portion of the excitation pulses 70, 71, 72 is shifted by a first time shift dT1 relative to the beginning of the envelope. A phase error of the phase response 81 hereby arises that is calculated as $$dphi=dT1*f$$

This phase error of the phase response 81 in FIG. 4 is graphically indicated by a shift of the phase responses 81 of the various RF pulses 70, 71, 72 to the right by dphi1 (RF pulse 70) and dphi2 (RF pulse 71, 72).

In the following it is explained in detail, with reference to FIG. 4, how conclusions about the phase errors dphi can be drawn by measurement of the relative phases of the various signals 76, 77, 78, and in particular how a first time shift dT1 can be calculated.

In the presently discussed embodiment, the phase of the second and third RF pulse 71, 72 is selected identically (i.e. phi2=phi3) to determine the first time shift dT1. See also in this regard the explanations with regard to FIG. 2. Therefore the phase errors of the second and third RF pulse 71, 72 are also identically designated as dphi2 and dphi3.

Furthermore, it is advantageous to not select all of the amplitudes of the gradient fields that are associated with the individual RF pulses to be the same:

gradient field 60a of the first RF pulse 70: amplitude Gs1;
gradient field 60b of the second RF pulse 71: amplitude Gs2;
gradient field 60c of the third RF pulse 72: amplitude Gs2.

The amplitude of the gradient fields is graphically indicated in FIG. 4.

If—as in the exemplary embodiment described in FIG. 4—the gradient field 60a (which is associated with the first radio-frequency pulse 70) and the gradient fields 60b, 60c (which are associated with the second radio-frequency pulse 71 and the third radio-frequency pulse 72) have different amplitudes, it is thus necessary that the radio-frequency (described by radio-frequency portion 80) of the first excitation pulse 70 has a different value than the radio-frequency described by radio-frequency portion 80 of the second and third RF pulse 71, 72. This is necessary so that the resonance condition for the spins in the same slice in the examination subject is satisfied in spite of different gradient fields 60a, 60b, 60c. Graphically, this is indicated by a lower value of the radio-frequency portion 80 of the first RF pulse 70 in comparison to the radio-frequency portion 80 of the second and third RF pulse 71, 72. Furthermore, due to the smaller shift of the radio-frequency relative to a reference frequency the first RF pulse 70 has a smaller change of the phase response 81 as a function of time than the second and third RF pulse 71, 72.

A first time shift dT1 of the beginning of the radio-frequency portion 80 relative to the envelope 82 produces a phase offset of dphi1 at the first RF pulse 70 and a phase offset of dphi2 at the second and third RF pulse 71, 72, as is indicated in FIG. 4.

It results from this that:

$$dphi1 = dT1*D*Gs1*\gamma,$$

from which it follows that:

$$phi1 = 0 + dphi1.$$

Furthermore, it results that:

$$dphi2 = dT1*D*Gs2*\gamma,$$

from which it follows that:

$$phi2 = \pi/2 + dphi2$$

The phases can be calculated from these by application of the argument function Arg to the individual spin signals 76, 77, 78. As discussed in detail with reference to FIG. 3, the spin signals 76, 77, 78 are to be associated with a first spin echo SE1, a second spin echo SE2 and a stimulated echo STE. The phases of these signals follow:

$$\mathrm{Arg}(SE1) = \pi/2 - (dphi1 - \pi - 2*dphi2) =$$
$$= -\pi/2 - dphi1 + dphi2,$$

$$\mathrm{Arg}(SE2) = -\pi/2 + dphi1,$$

and $$\mathrm{Arg}(STE) = \pi/2 - (dphi1 - \pi - 2*dphi2) =$$
$$= +3/2\pi - dphi1 + 2dphi2 =$$
$$= -\pi/2 - dphi1 + 2dphi2.$$

For example, within the scope of a calibration measurement to synchronize various components of a magnetic resonance system it is possible to measure the phase difference dPHI between the secondary spin echo SE2 (spin signal 78) and the stimulated spin echo STE (spin signal 77).

$$dPHI = \mathrm{Arg}(STE) - \mathrm{Arg}(SE2) =$$
$$= 2*dphi2 - 2*dphi1.$$

From this formula for dPHI it is possible to calculate the time shift:

$$dPHI = 2*(dphi2 - dphi1) =$$
$$= 2*dT1*D*(Gs2 - Gs1)*\gamma,$$

from which it results that:

$$dT1 = dPHI/(2*D*(Gs2-Gs1)*\gamma).$$

This formula enables the first time shift dT1 between the radio-frequency portion 80 and the envelope 81 of RF pulses to be determined by implementation of an MR acquisition sequence as it has been explained with regard to FIG. 4. This occurs by the detection of three spin signals 76, 77, 78. By suitable selection of the output parameters and measurement of a phase difference it is possible to determine the unknown parameters of the first time shift dT1.

While a possibility to determine the first time shift dT1 has been discussed in the preceding with regard to FIG. 4, it should be clear that many other corresponding possibilities exist to determine dT1. The exemplary embodiment discussed in FIG. 4 is therefore not to be construed as limiting. It is hereby merely essential that it is possible—from a series of known parameters such as amplitude, slice selection gradients and radio-frequency and a series of measured parameters such as the relative phase positions—to determine unknown parameters of the MR acquisition sequence, in particular the time shift dT1. In other words: it is necessary to set up an equation system of the participating variables such that it is sufficiently determined in order to achieve an unambiguous solution. This means that such a sufficiently large number of known parameters must always be present such that a solution is accessible.

At the same time it can be advantageous if the parameter space is reduced by equating specific participating variables in order to enable a simple solution of the equation system. With regard to FIG. 2, this occurs by the selection of identical amplitudes GS2 of the gradient fields 60b, 60c that also relate to the second and third RF pulse 71, 72.

For example, it would also be possible to select the amplitude of the gradient fields 60b and 60c differently. The corresponding formulas for the phase position of the various signals would then be more complicated. In particular, however, it can be advantageous if at least two of the three gradient fields 60a, 60b, 60c have the same amplitudes in order to remove a parameter from the equation system in such a manner. With regard to FIG. 3, it can also be possible to use other spin signals (instead of the second spin signal 77 and the third spin signal 78, i.e. the stimulated spin echo and the secondary spin echo) to determine the first time shift dT1, for instance the first spin signal 76. From FIG. 3 it can be seen that an additional spin signal in the form of a spin echo can be detected at a later point in time. The further diversification of the coherence curve 50 is not completely recorded in FIG. 3, such that additional, higher spin echoes are not graphically indicated. However, in principle it is merely necessary to measure signals that enable a conclusion of the parameters of the exciting or, respectively, deflecting radio-frequency pulses 70, 71, 72.

The RF pulses of an MR acquisition sequence to determine the time shift between different components of the MR acquisition sequence are shown in FIG. 5. The RF pulses correspond to the RF pulses discussed with regard to FIGS. 2, 3 and 4. However, in particular the gradient fields 60a, 60b, 60c that respectively belong to the RF pulses 70, 71, 72 are shifted by a second time shift dT2 relative to the respective envelope. As was already discussed with regard to FIG. 4, the slice selection amplitudes of the individual RF pulses are selected to be of different levels:

gradient field 60a of the first RF pulse 70: amplitude Gs1;

gradient field 60b of the second RF pulse 71: amplitude Gs2;

gradient field 60c of the third RF pulse 72: amplitude Gs2.

If the beginning of the respect slice selection gradient 89 is now time-shifted by dT2 relative to the beginning of the respective envelope 82 (i.e. the amplitude modulation signal), additional gradient moments M are thus generated on the slice selection axis. These generate an additional phase rotation on the transverse component of the magnetization with regard to dT2=0:

$$dphi = D*M*\gamma.$$

The effect of the time shift on the dephasing of the coherence curve is ignored since this leads to a reduction of the amplitude of the spin signals but the phase of the spin signals does not vary. For example, it is possible to minimize the signal reduction by a correspondingly small selection of the excited slice thickness.

The various gradient moments in an acquisition sequence as it is shown in FIG. 5 are now explained in detail. An additional moment dM is generated between the first and second RF pulse 70, 71:

$$dM = M2 - M1 = (Gs2 - Gs1)*dT2,$$

which leads to a corresponding phase rotation of the transverse components:

$$dphi1 = D*dM*\gamma = D*dT2*(Gs2-Gs1)*\gamma.$$

The moments M1 and M1 [sic] are shown dark in FIG. 5. This phase rotation dphi1 can be considered as an additional phase of the first RF pulse with regard to the effect on the transverse components of the magnetization.

No additional gradient moment arises between the second and third RF pulse 71, 72 since both gradient amplitudes are of equal magnitude. The corresponding gradient moments after the second RF pulse 71 and before the third RF pulse 72 have different algebraic signs.

However, an additional moment of $$-M2 = -Gs2*dT2,$$

arises after the third RF pulse 72, which in turn generates a phase rotation dphi3 of the transverse components:

$$dphi3 = -D*dT2*Gs2*\gamma.$$

As was presented further above with regard to FIG. 2, the additional phase dphi3 pertains to both the stimulated spin echo STE and the secondary spin echo SE2. The phases of the spin signals 76, 77, 78 then read:

$$Arg(SE1) = \pi/2 - (dphi1 - \pi - 2*dphi2)$$
$$= -\pi/2 - dphi1,$$

$$Arg(SE2) = -\pi/2 + dphi1 + dphi3,$$

$$Arg(STE) = \pi/2 + \pi + dphi3)$$
$$= -\pi/2 + dphi3.$$

As was already discussed with regard to FIG. 4, it is possible to measure the dPHI phase difference between the secondary spin echo and the stimulated spin echo. This reads:

$$dPHI = Arg(STE) - Arg(SE2) = dphi1.$$

Insertion yields:

$$dPHI = dT2*D*(Gs2-Gs1)*\gamma,$$

which is why the second time shift dT2 between the slice selection gradients 89 and the envelope 82 yields:

$$dT2 = dPHI/(D*(Gs2-Gs1)*\gamma).$$

As explained with regard to FIG. 4, the exemplary embodiment of FIG. 5 is not to be construed as limiting. In particular, the parameters of the RF pulses 70, 71, 72 or the measured spin signals can have different parameters or, respectively, can be different. Only a sufficiently high number of parameters must necessarily be known, such that the arising equation system is sufficiently designed to determine the second time shift dT2. In particular, to determine the second time shift dT2 between the envelope 82 and the slice selection gradient 89 it was not used in FIG. 5 that the second RF pulse 71 and the third RF pulse 72 have the same phase. This is a difference relative to the example discussed above with regard to FIG. 3 to determine the first time shift dT1 between the radio-frequency portion 80 and the envelope 82. However, it would also be possible to select the phases of the three RF pulses 70, 71, 72 with regard to FIG. 4 to determine the first time shift dT1.

With reference to FIGS. 4 and 5, it was explained in the preceding how it is possible in principle to draw conclusions about the time shifts dT1, dT2 from the measurement of the phase shift between two signals 71, 72. With regard to FIG. 6, a method is described in the following that particularly simply enables the phase shift dPHI to be suitably determined in order to obtain the time shifts dT1, dT2. For this, the first RF pulse 70 is charged with an additional phase ε that is varied in small increments in a large value range. For each ε, an MR experiment is implemented with three RF pulses and detection or, respectively, measurement of at least the spin echoes SE2 and STE, as is described in detail in the preceding with regard to FIGS. 4 and 5. The phase difference Arg(SE2)−Arg(STE) between the secondary spin echo SE2 and the stimulated spin echo STE is respectively determined. From the measured data, that ε is sought at which SE2 and STE are in parallel, meaning that the second spin echo and the stimulated spin echo have identical phases or, respectively, the phase difference is minimized. As is explained in the following, this directly allows a determination of the first time shift dT1 (second time shift dT2) as was explained with regard to FIG. 4 (FIG. 5).

For the determination of dT1, given additional charging of the first RF pulse 70 with the phase ε the phases of the spin signals SE2 and STE respectively result in:

$$Arg(SE2) = -\pi/2 + \epsilon + dphi1,$$

$$Arg(STE) = -\pi/2 - \epsilon - dphi1 + 2dphi2.$$

The parameter ε is varied until it is valid that:

$$Arg(SE2) = Arg(STE).$$

Insertion yields the equation:

$$-\pi/2+\epsilon+dphi1=-\pi/2-\epsilon-dphi1+dphi2,$$

and from this it follows—as a comparison with the Specification with regard to FIG. 4 yields:

$$\varepsilon = (-2dphi1 + 2dphi2)$$
$$= 2*(dphi2 - phi1)$$
$$= dPHI.$$

dPHI is defined as described in the preceding with regard to FIG. 4.

To determine dT2, for the phases of the individual echoes SE2 and STE it applies that:

$$\mathrm{Arg}(SE2) = -\pi/2 + \varepsilon + dphi1 + dphi3,$$
$$\mathrm{Arg}(STE) = \pi/2 - \varepsilon + \pi + dphi3 =$$
$$= -\pi/2 - \varepsilon + dphi3.$$

$\epsilon$ is in turn varied until $$\mathrm{Arg}(SE2)=\mathrm{Arg}(STE).$$

Insertion delivers the equation:

$$-\pi/2+\epsilon+dphi1+dphi3=-\pi/2-\epsilon+dphi3,$$

$$\epsilon+dphi1=-\epsilon,$$

and from this it follows—as a comparison with the Specification with regard to FIG. 5 yields:

$$\epsilon=\tfrac{1}{2}*dphi1=\tfrac{1}{2}*dPHI.$$

It is possible to define the interval $d\epsilon$ with which $\epsilon$ is varied using the desired temporal resolution R. The higher the temporal resolution R, the more precisely that the synchronization of the various components takes place. At the same time, however, a synchronization according to the shown method can take longer.

With regard to dT1, the necessary interval for a given temporal resolution results as:

$$d\epsilon=R*D*Gs\gamma$$

With regard to dT2, the necessary interval for a given temporal resolution results as:

$$d\epsilon=R*D*(Gs2-Gs1)\gamma$$

FIG. 7 is a flow diagram according to a method according to an exemplary embodiment of the present invention for synchronization of various components of an MR system. The method begins in Step 700. In Step 701, a pre-calibration is initially implemented. A pre-calibration can have the purpose of eliminating at least one of the time shifts dT1, dT2 (discussed in the preceding) respectively between the envelope 82 and the radio-frequency portion 80 or, respectively, between the envelope 82 and the slice selection gradient 89. Namely, if either the first time shift dT1 or the second time shift dT2 is already removed by a pre-calibration within the scope of Step 701, the additional steps of the method according to the invention can thus be implemented without limitations that result—for instance—from the overlapping of effects due to a simultaneous first and second time shift. An overlap of various effects that occur due to the two different time shifts dT1, dT2 can be precluded. For example, a pre-calibration according to Step 701 can occur in the development process by a suitable analysis of the participating MR system components. This has already been described in the preceding.

The selection of the initial parameters for a synchronization acquisition sequence (as they have been discussed with regard to FIGS. 2-5) can subsequently occur in Step 702. For example, the amplitudes of different slice selection gradients 89 can be selected differently or identically. Moreover, which of the various spin signals are used for measurement can be selected. This means that the parameters of the RF pulses 70, 71, 72 can be concluded by various spin signals. It is also possible that four or five corresponding RF pulses are used, for example instead of three RF pulses 70, 71, 72. The number or the position of the spin signals can then be varied. More complex workflows of the coherence curve 50 are possible than discussed with regard to FIG. 3.

In particular, an initial parameter for the phase position of one of the RF pulses can be selected in Step 702. As discussed with regard to FIG. 6, for example, the phase of the first RF pulse 70 can be varied incrementally in that a phase E is impressed. The phase E can additionally be varied for intrinsic phase of the first RF pulse 70. In Step 703 it can thus be checked whether the phases of at least two signals are identical. For example, as described with regard to FIG. 3 it can be checked whether the phase of a second spin signal 77 and a third spin signal 78 are identical. The second spin signal 77 and the third spin signal 78 hereby correspond to a stimulated spin echo STE and a secondary spin echo SE2. If it is detected by a measurement in Step 703 that the phases of the stimulated spin echo STE and the secondary spin echo SE2 are not identical, the phase E can be incremented so that the first RF pulse 70 has a different phase. This occurs within the scope of Step 704.

Step 703 and Step 704 are repeated until it is detected in the measurement that the phase of two spin signals is the same. Namely, if it is detected in Step 703 that the phase of two spin signals is the same, in Step 705 a synchronization of the corresponding components of the MR system can occur based on the known phase $\epsilon$. The corresponding components of the MR system can be a radio-frequency signal generator 20, a gradient unit 23 and an amplitude modulation unit 24.

After the components of the MR system that are responsible for the generation of the RF pulses 70, 71, 72 and slice selection gradients 89 have been temporally synchronized in Step 705, the actual measurement can be implemented in Step 706. The method subsequently comes to an end in Step 707.

Exemplary embodiments of the invention can be used to synchronize components of MR systems. One field of application is MR systems with non-Cartesian sampling, without the exemplary embodiments being limited to this.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for time synchronization of multiple components with each other in a magnetic resonance system, comprising:

operating multiple components of a magnetic resonance data acquisition unit to generate a series of amplitude-modulated radio-frequency (RF) pulses and associated gradient fields, each of said amplitude modulated RF pulses comprising a signal envelope of that respective pulse that encompasses an RF portion at a frequency matched to a respective frequency of the nuclear spins, and thereby exciting said nuclear spins and deflecting magnetization of said nuclear spins in a slice of a subject in the data acquisition unit;

detecting at least two spin signals that result from the deflection of the magnetization of said nuclear spins;

in a processor, determining a phase difference between two of said spin signals;

in said processor, determining, from said phase difference, at least one time shift between two variables that are generated by different components of said data acquisition unit among said multiple components, selected from the group consisting of said envelope of said amplitude-modulated RF pulses, said RF portion of said amplitude-modulated RF pulses, and one or more of said gradient fields; and from said processor, synchronizing said different components dependent on said at least one time shift.

2. A method as claimed in claim 1, comprising operating said data acquisition unit to generate said RF pulses and said associated gradient fields in said slice that is shifted by a predetermined distance with respect to a reference slice at which said magnetization is deflected by a reference frequency.

3. A method as claimed in claim 1, wherein each of said RF pulses has a deflection angle of said magnetization and a phase position associated therewith, and selecting the respective deflection angles to cause only a portion of said magnetization in said slice to be deflected, with said radio-frequency pulses and said associated gradient fields causing at least one parameter to assume at least two different values, said at least one parameter being selected from the group consisting of the respected deflection angles of the RF pulses, the respective phase positions of the RF pulses, and respective amplitudes of said gradient fields.

4. A method as claimed in claim 3, wherein said radio-frequency pulses and associated gradient fields cause said at least one parameter to assume a same value at least twice.

5. A method as claimed in claim 1, comprising:
incrementally varying a phase position of at least one of said radio-frequency pulses to minimize said phase difference in the determination of said at least one time shift.

6. A method as claimed in claim 1, comprising deflecting said magnetization by radiating a first RF pulse with an associated first gradient field, a second RF pulse with an associated second gradient field, and a third RF pulse with an associated third gradient field, and detecting said spin signals as a first spin echo, a second spin echo, and a stimulated spin echo.

7. A method as claimed in claim 6, wherein said first gradient field has a first gradient amplitude Gs1, and wherein said second and third gradient fields have a same second gradient amplitude Gs2.

8. A method as claimed in claim 7, comprising calculating a first time shift dT1 between an envelope of the amplitude-modulated RF pulses and the RF portion of the amplitude-modulated RF pulses according to:

$$dT1 = dPHI/(2D(Gs2-Gs1)\gamma)$$

wherein dPHI is the phase difference between the phase of the second detected spin echo and the phase of the stimulated spin echo; wherein D is the distance of the slice from the reference slice; and wherein $\gamma$ is the gyromagnetic ratio; wherein the phase positions of the first and second radio-frequency pulse are selected identically.

9. A method as claimed in claim 8, comprising calculating a second time shift dT2 between the gradient fields and the RF portion of the amplitude-modulated RF pulses according to:

$$dT2 = dPHI/(D(Gs2-Gs1)\gamma).$$

10. A magnetic resonance system comprising:
a magnetic resonance data acquisition unit comprising a plurality of components including radio-frequency coils and gradient coils;

a control unit configured to operate the plurality of components of the magnetic resonance data acquisition unit to generate a series of amplitude-modulated RF pulses with said RF coils and associated gradient fields with said gradient coils, each of said amplitude modulated RF pulses comprising a signal envelope of that respective pulse that encompasses an RF portion at a frequency matched to a respective frequency of the nuclear spins, and thereby to excite said nuclear spins to deflect magnetization of nuclear spins in a slice of a subject in the data acquisition unit;

said control unit being configured to operate said magnetic resonance data acquisition unit to detect at least two spin signals that result from the deflection of the magnetization of said nuclear spins;

a processor configured to determine a phase difference between two of said spin signals;

said processor being configured to determine, from said phase difference, at least one time shift between two variables that are generated by different components of said data acquisition unit among said plurality of components, selected from the group consisting of said envelope of said amplitude-modulated RF pulses, said RF portion of said amplitude-modulated RF pulses, and one or more of said gradient fields; and said processor being configured to synchronize said different components dependent on said at least one time shift.

* * * * *